United States Patent
Omote et al.

(10) Patent No.: US 9,335,282 B2
(45) Date of Patent: May 10, 2016

(54) X-RAY TOPOGRAPHY APPARATUS

(71) Applicant: Rigaku Corporation, Akishima-Shi, Tokyo (JP)

(72) Inventors: Kazuhiko Omote, Akiruno (JP); Yoshinori Ueji, Akishima (JP); Ryuji Matsuo, Hino (JP); Tetsuo Kikuchi, Tachikawa (JP)

(73) Assignee: RIGAKU CORPORATION (JP)

( * ) Notice: Subject to any disclaimer, the term of this patent is extended or adjusted under 35 U.S.C. 154(b) by 300 days.

(21) Appl. No.: 13/845,744

(22) Filed: Mar. 18, 2013

(65) Prior Publication Data
US 2013/0259200 A1 Oct. 3, 2013

(30) Foreign Application Priority Data

Apr. 2, 2012 (JP) .................................. 2012-083680

(51) Int. Cl.
*G01N 23/207* (2006.01)
*G21K 1/06* (2006.01)
*B82Y 10/00* (2011.01)

(52) U.S. Cl.
CPC .............. *G01N 23/207* (2013.01); *B82Y 10/00* (2013.01); *G21K 1/062* (2013.01)

(58) Field of Classification Search
CPC .............. G01N 23/207; G01N 23/205; G01N 23/2055; G01N 2223/0561; G01N 2223/0566; G21K 1/062
See application file for complete search history.

(56) References Cited

U.S. PATENT DOCUMENTS

| | | | | |
|---|---|---|---|---|
| 6,226,349 B1 * | 5/2001 | Schuster et al. | ................. | 378/84 |
| 6,278,764 B1 * | 8/2001 | Barbee et al. | .................... | 378/84 |
| 6,529,578 B1 * | 3/2003 | Taguchi et al. | ................. | 378/84 |
| 2004/0066894 A1 | 4/2004 | Holz et al. | | |
| 2004/0066896 A1 | 4/2004 | Fujinawa et al. | | |
| 2008/0273662 A1 * | 11/2008 | Yun et al. | ........................ | 378/74 |

(Continued)

FOREIGN PATENT DOCUMENTS

| | | | |
|---|---|---|---|
| DE | 3442061 A1 | 5/1986 | |
| DE | 4407278 A1 | 9/1995 | |

(Continued)

OTHER PUBLICATIONS

Partial Translation of the Office Action for Japanese Patent Application No. 2012-083680 (Mailing Date: Mar. 24, 2015).

(Continued)

*Primary Examiner* — Glen Kao
(74) *Attorney, Agent, or Firm* — Cantor Colburn LLP

(57) ABSTRACT

Provided is an X-ray topography apparatus capable of separating a desired characteristic X-ray which enters a sample from an X-ray which is radiated from an X-ray source, and increasing an irradiation region of the desired characteristic X-ray. The X-ray topography apparatus includes: the X-ray source for radiating the X-ray from a fine focal point, the X-ray containing a predetermined characteristic X-ray; an optical system including a multilayer mirror with a graded multilayer spacing which corresponds to the predetermined characteristic X-ray, the optical system being configured to cause the X-ray reflected on the multilayer mirror to enter the sample; and an X-ray detector for detecting a diffracted X-ray. The multilayer mirror includes a curved reflective surface having a parabolic cross section, and the fine focal point of the X-ray source is provided onto a focal point of the curved reflective surface.

6 Claims, 3 Drawing Sheets

(56) References Cited

U.S. PATENT DOCUMENTS

| | | |
|---|---|---|
| 2011/0268252 A1 | 11/2011 | Ozawa et al. |
| 2012/0014508 A1* | 1/2012 | Wormington et al. .......... 378/71 |

FOREIGN PATENT DOCUMENTS

| | | |
|---|---|---|
| DE | 19833524 A1 | 2/2000 |
| DE | 10107914 A1 | 9/2002 |
| DE | 102008049163 A1 | 4/2010 |
| GB | 2181630 B | 1/1989 |
| JP | 4944151 | 12/1974 |
| JP | 5024232 | 7/1975 |
| JP | H04174349 A | 6/1992 |
| JP | 2001021507 A | 1/2001 |
| JP | 2002310950 A | 10/2002 |
| JP | 2005512050 A | 4/2005 |
| JP | 2008082939 A | 10/2008 |
| WO | 9522758 A1 | 8/1995 |
| WO | 03048752 A1 | 6/2003 |

OTHER PUBLICATIONS

German Office Action corresponding to Application No. 102013004503.7; Dated Mar. 9, 2016.

* cited by examiner

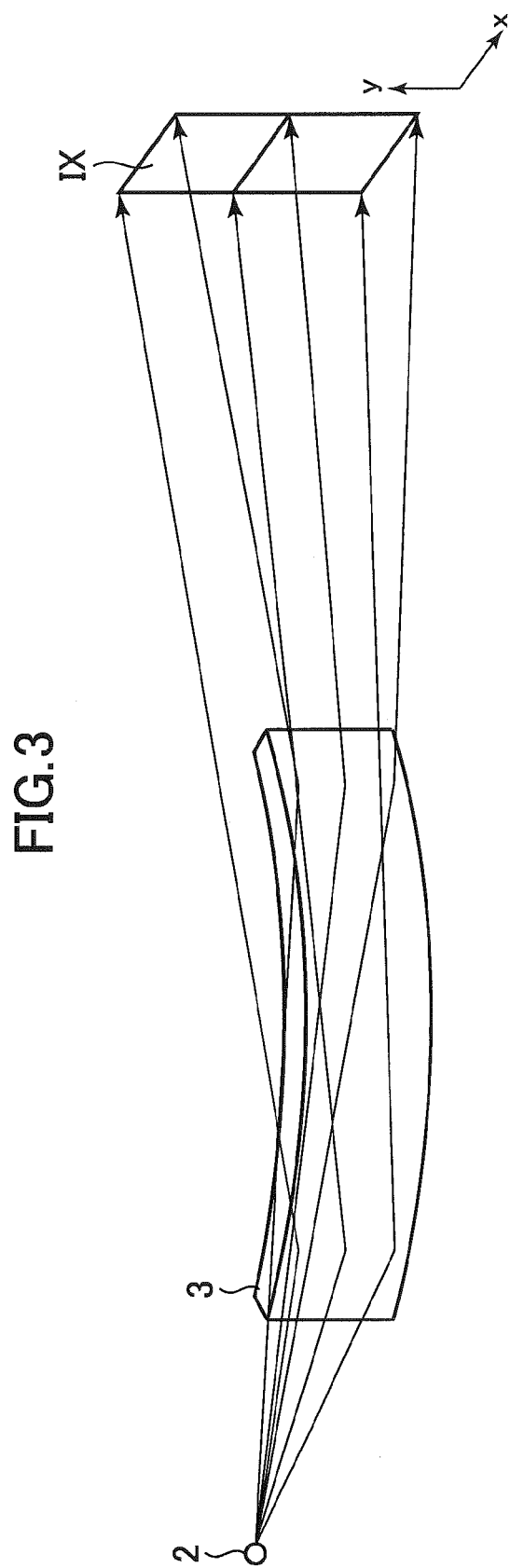

X-RAY TOGRAPHY APPARATUS

CROSS-REFERENCE TO RELATED APPLICATION

The present application claims priority under 35 U.S.C. §119 to Japanese application 2012-083680, filed on Apr. 2, 2012, the entire content of which is incorporated herein by reference.

BACKGROUND OF THE INVENTION

1. Field of the Invention

The present invention relates to an X-ray topography apparatus, and more particularly, to an X-ray topography apparatus using a multilayer mirror.

2. Description of the Related Art

An X-ray topography apparatus is an apparatus for observing, as an X-ray diffraction image, various crystal defects such as dislocations and precipitation in a single crystal, which are hard to observe when using general optical means. A diffraction phenomenon occurs when a sample crystal is placed so that lattice planes having a plane spacing "d" satisfy the Bragg's law "$2d \cdot \sin \theta_n = n\lambda$" with respect to a wavelength "$\lambda$" of an incident X-ray. When the above-mentioned crystal defects are present within an irradiation region of the incident X-ray, the X-ray diffraction image has a difference in intensity between the crystal defect portion and the other portion. The X-ray diffraction image obtained by detecting the difference in intensity through use of a detector is referred to as "X-ray topographic image".

The X-ray topography apparatus uses the Lang method, the Berg-Barrett method, the double crystal method, and other methods. The Lang method is a method of examining a distribution of defects in a crystal through imaging in the transmission geometry, and is most widely used thus far. The Berg-Barrett method is a method of examining and observing a crystal surface through imaging in the reflection geometry. The double crystal method is a method of diffracting an X-ray emitted from an X-ray source on a first crystal to obtain a monochromatized and collimated X-ray beam, which is caused to enter a sample crystal as a second crystal. The conventional X-ray topography apparatus uses a fine-focus X-ray source which may be regarded as a point X-ray source, and has a slit arranged between the X-ray source and the sample. With this structure, the angle of divergence of the X-ray which enters the sample is restricted, to thereby obtain a substantially collimated X-ray.

SUMMARY OF THE INVENTION

Through use of the slit, the X-ray which enters the sample can be changed to a substantially collimated X-ray. In order to restrict the angle of divergence of the X-ray to the extent that the X-ray can be regarded as a substantially collimated X-ray, however, the slit width needs to be reduced to a predetermined value, resulting in a limited irradiation region of the incident X-ray which enters the sample. Further, a predetermined distance needs to be secured between the X-ray source and the slit, and as a result, the brightness of the incident X-ray is decreased as well.

In the X-ray source, there are generated continuous X-rays and characteristic X-rays unique to a target (metal) used for an anode. For example, in a case of causing a diffraction phenomenon through use of a desired characteristic X-ray as the incident X-ray, the situation that other X-rays enter the sample to cause the diffraction phenomenon is not desired from the viewpoint of taking an X-ray topographic image with higher accuracy. This is because, when the incident X-ray contains a component of the continuous X-ray, the X-ray topographic image to be taken is affected by the background due to the Laue diffraction of the continuous X-ray. Further, when another characteristic X-ray slightly different in wavelength enters the sample, the X-ray topographic image to be taken contains an X-ray diffraction image formed from the another characteristic X-ray. In a case of using the conventional Lang method, in order to separate a desired characteristic X-ray (for example, $K\alpha_1$) from another characteristic X-ray (for example, $K\alpha_2$), a vertically elongated slit needs to be arranged in the vicinity of the sample to prevent the situation that the resultant X-ray topographic image contains the unwanted diffraction image formed from the another characteristic X-ray.

Conventionally, various technologies have been used for separating a desired characteristic X-ray from another characteristic X-ray. Japanese Utility Model Examined Publication No. Sho 49-44151 (hereinafter referred to as "Patent Literature 1") and Japanese Utility Model Examined Publication No. Sho 50-24232 (hereinafter referred to as "Patent Literature 2") disclose a Lang X-ray diffraction camera using a curved monochromator crystal. In Patent Literatures 1 and 2, a part of the X-ray generated from the X-ray source enters the curved monochromator crystal, and is converged and focused by the curved monochromator crystal. In this manner, the desired characteristic X-ray is separated from another X-ray.

In Patent Literature 1, a first slit (slit 3) is provided at a focusing position of the characteristic X-ray $K\alpha_1$. The characteristic X-ray $K\alpha_1$ passes through the first slit and enters the sample. On the other hand, the characteristic X-ray $K\alpha_2$ slightly different in wavelength is focused at a position in the vicinity of the first slit, and hence the characteristic X-ray $K\alpha_2$ is blocked by the first slit, thereby preventing the propagation to the sample. Another X-ray also different in wavelength is absorbed or scattered by the curved monochromator crystal, thereby preventing the propagation to the sample. In this manner, the characteristic X-ray $K\alpha_1$ is separated from the other X-rays, but the characteristic X-ray $K\alpha_1$ after passing through the first slit propagates while diverging from the focal point. A second slit (slit 5) is arranged in front of the sample, and the second slit restricts the angle of divergence of the characteristic X-ray $K\alpha_1$ within a predetermined range. In this case, the characteristic X-ray $K\alpha_1$ does not need to be a substantially collimated X-ray, and therefore the slit width of the second slit can be increased so as to set the angle of divergence within the predetermined range, with the result that the irradiation region of the incident X-ray which enters the sample can be increased. In this X-ray diffraction camera, the characteristic X-ray $K\alpha_1$ which enters the sample has the angle of divergence within the predetermined range, and accordingly, even when the sample is curved in some degree, the entire surface can be imaged. However, when the X-ray is monochromatized by such a method as described above, only a part of the incident characteristic X-ray $K\alpha_1$ contributes to the diffraction due to the divergence of the incident characteristic X-ray $K\alpha_1$, thus leading to a problem in that the brightness of the X-ray on an X-ray imaging plate becomes extremely lower and the measurement time becomes longer.

In Patent Literature 2, the sample is placed at the focusing position of the characteristic X-ray $K\alpha_1$, and a first slit (slit 6) is provided in front of the sample. Similarly to Patent Literature 1, the characteristic X-ray $K\alpha_1$ is separated from the other X-rays through the first slit. A second slit (slit 8) is provided in front of an X-ray imaging plate 7, and accordingly the X-ray topographic image can be taken with higher image quality. In this X-ray diffraction camera, however, the sample is placed at the focusing position of the characteristic X-ray $K\alpha_1$, and hence there arises a problem of the limited irradiation region of the incident X-ray. In this X-ray diffraction camera, the incident characteristic X-ray $K\alpha_1$ converges on the focal point which is located inside the sample, and accordingly, even when the sample is curved in some degree, the entire surface can be imaged. Also in this case, however, similarly to the case of Patent Literature 1, there is a problem in that the brightness of the X-ray on the X-ray imaging plate becomes extremely lower.

In the Lang X-ray diffraction camera according to Patent Literature 1 or 2, the X-ray is temporarily converged on the focal point by the curved monochromator crystal, and it is therefore difficult to increase the irradiation region of the X-ray which enters the sample and to satisfy the condition for simultaneously causing diffraction over this region. Further, in the technology according to Patent Literature 1 or 2, the slit is provided in front of the sample, and hence this technology cannot be applied to the Berg-Barrett method or has significant restrictions even when the technology is applied.

Japanese Patent Application Laid-open No. 2008-82939 (hereinafter referred to as "Patent Literature 3") discloses an improved technology of a double crystal X-ray topography apparatus. A first crystal 1 and a second crystal 2 are placed on a highly stable surface table 3, and an X-ray source 5 is arranged together with a slit 6 on a movable scanning base 7. A mechanical insulation process is performed at a position between the surface table 3 and the scanning base 7, and accordingly stable scanning can be performed. In this X-ray topography apparatus, the slit is arranged between the first crystal and the X-ray source, thereby restricting the angle of divergence of the X-ray which enters the first crystal. Through use of the slit 6, however, the brightness of the X-ray which enters the first crystal 1 becomes lower. After the X-ray passes through the slit, the X-ray is monochromatized and collimated by the first crystal 1, and hence the brightness of the incident X-ray which enters the second crystal 2 as the sample becomes even lower. Further, the slit 6 is provided so as to restrict the angle of divergence of the X-ray to the extent that the X-ray can be regarded as a substantially collimated X-ray, and therefore needs to be arranged away from the X-ray source 5 with a predetermined distance therebetween. In fact, the X-ray source 5 and the slit 6 need to be arranged on the scanning base 7, which leads to an increase in scale of the apparatus and a limitation on the degree of freedom of design.

The present invention has been made in view of the above-mentioned problems, and therefore has an object to provide an X-ray topography apparatus capable of separating a desired characteristic X-ray which enters a sample from an X-ray which is radiated from an X-ray source, and increasing an irradiation region of the desired characteristic X-ray which enters the sample and contributes to diffraction.

(1) In order to solve the above-mentioned problems, according to an exemplary embodiment of the present invention, there is provided an X-ray topography apparatus, including: an X-ray source for radiating an X-ray from a fine focal point, the X-ray containing a predetermined characteristic X-ray; an optical system including a multilayer mirror with a graded multilayer spacing which corresponds to the predetermined characteristic X-ray, the optical system being configured to cause the X-ray reflected on the multilayer mirror to enter a sample; and an X-ray detector for detecting a diffracted X-ray, which is generated through the sample.

The multilayer mirror includes a curved reflective surface having a parabolic cross section, and the fine focal point of the X-ray source is provided onto a focal point of the curved reflective surface.

(2) The X-ray topography apparatus according to the above-mentioned Item (1) may further include a rotational driving system having the X-ray source and the optical system arranged thereon, the rotational driving system being rotationally movable with respect to the sample.

The rotational driving system may be configured to move the X-ray source and the optical system through selection of one of a transmission geometry for transmission topography and a reflection geometry for reflection topography, and to further move the X-ray source and the optical system in the selected one of the transmission geometry and the reflection geometry so that the X-ray satisfies a desired diffraction condition with respect to the sample.

(3) In the X-ray topography apparatus according to the above-mentioned Item (1) or (2), the optical system may further include a single crystal monochromator arranged between the multilayer mirror and the sample, the single crystal monochromator corresponding to a wavelength of the predetermined characteristic X-ray.

(4) In the X-ray topography apparatus according to any one of the above-mentioned Items (1) to (3), the multilayer mirror may have surface figure error from the ideal surface is 10 arcsec or less.

The present invention provides an X-ray topography apparatus capable of separating a desired characteristic X-ray which enters a sample from an X-ray which is generated from an X-ray source, and increasing an irradiation region of the desired characteristic X-ray which enters the sample and contributes to diffraction.

BRIEF DESCRIPTION OF THE DRAWINGS

In the accompanying drawings:

FIG. 3 is a schematic view illustrating the structure of the multilayer mirror according to the embodiment of the present invention.

DETAILED DESCRIPTION OF THE INVENTION

In the following, an embodiment of the present invention is described in detail with reference to the drawings. Note that, the figures to be referred to below only illustrate this embodiment, and the scale of the figures and the scale described in this embodiment are not necessarily identical with each other.

Figure 1:
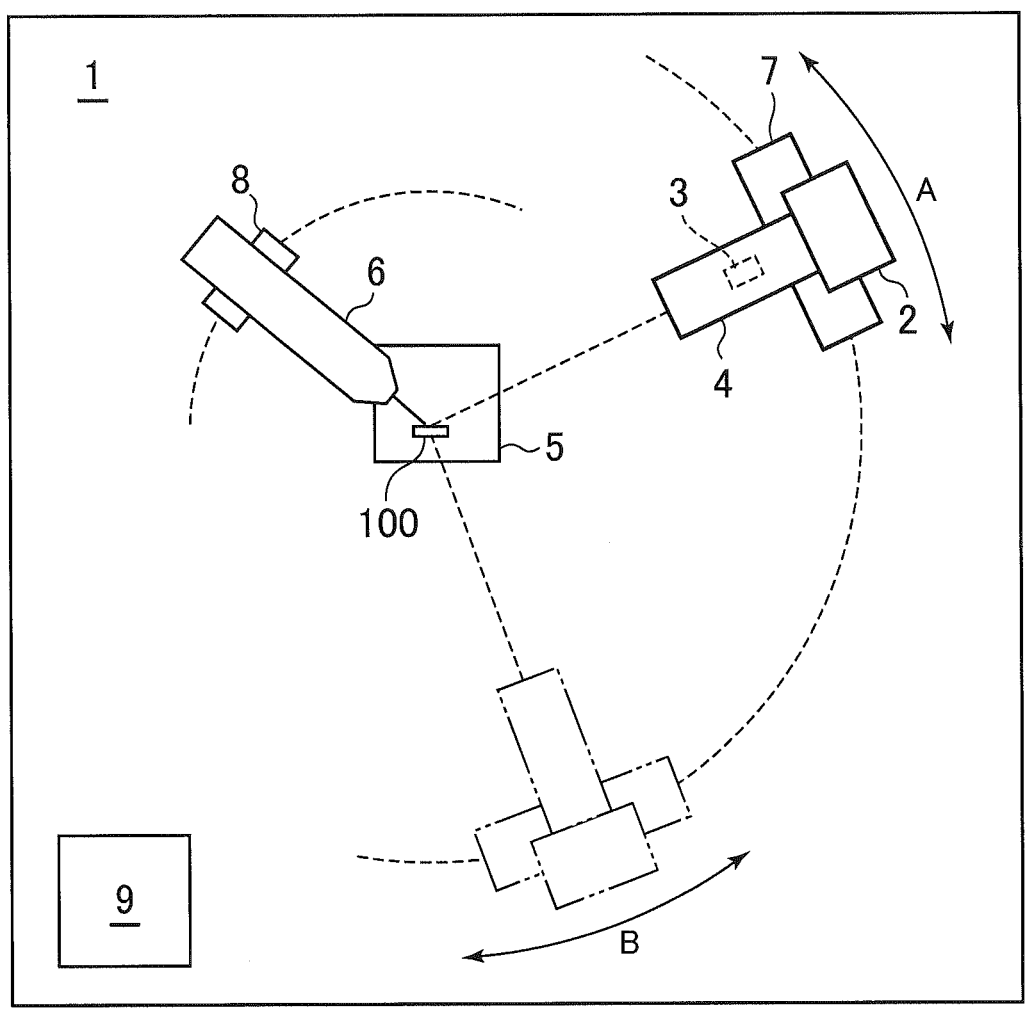
FIG. 1 is a schematic view illustrating a structure of an X-ray topography apparatus according to an embodiment of the present invention.

FIG. 1 is a schematic view illustrating a structure of an X-ray topography apparatus 1 according to the embodiment of the present invention. The X-ray topography apparatus 1 according to this embodiment includes an X-ray source 2 for radiating an X-ray containing a predetermined characteristic X-ray, an optical system 4 which includes a multilayer mirror 3 and is configured to cause the X-ray reflected on the multilayer mirror 3 to enter a sample 100, a sample table 5 for supporting the sample 100, an X-ray detector 6 for detecting a diffracted X-ray, which is generated through the sample 100, a first rotational driving system 7 which has the X-ray source 2 and the optical system 4 arranged thereon and is capable of angular movement with respect to the sample 100, a second rotational driving system 8 which has the X-ray detector 6 arranged thereon and is capable of angular movement with respect to the sample 100, and a control/analysis unit 9 for controlling X-ray topography measurement and analyzing measurement data. Note that, the sample 100 refers to a single crystal sample.

The features of the X-ray topography apparatus 1 according to this embodiment reside in that the X-ray source 2 is a fine-focus X-ray source which may be regarded as a point X-ray source, and that the X-ray radiated from the X-ray source 2 is monochromatized and collimated by the multilayer mirror 3. The X-ray monochromatized and collimated by the multilayer mirror 3 can be caused to enter the sample, and an X-ray diffraction image (topographic image) formed from a desired characteristic X-ray can be taken without using a geometric slit.

In the following, the structure of the X-ray topography apparatus 1 according to this embodiment is described.

The X-ray source 2 uses a metal such as copper (Cu) or molybdenum (Mo) as a target. Electrons emitted from a cathode are caused to impinge on the target, and X-rays are radiated in all directions from the region in which the electrons impinge on the target. The X-ray radiated from the X-ray source 2 contains a characteristic X-ray (for example, $CuK\alpha_1$ or $MoK\alpha_1$) unique to the metal used as the target. The shape of the region is determined based on the shape of the cathode, but the region is a fine focal point, and due to the fact that the fine focal point is sufficiently small, the X-ray source 2 may be regarded substantially as the point X-ray source. Regardless of whether to use Cu or Mo as the target of the X-ray source 2, the fine focal point has a circular shape with a diameter of 0.07 mm. The size of the fine focal point is not limited thereto, and may be any size which is small enough to obtain a predetermined resolution of the X-ray topographic image. For example, the applicable size of the fine focal point (in both the vertical and horizontal directions) is 0.3 mm or less. Note that, the size of the fine focal point is desirably 0.2 mm or less, more desirably 0.1 mm or less. Further, Cu or Mo is used as the target of the X-ray source 2, but the metal to be used as the target is not limited thereto, and may be applied depending on the crystal as the sample. For example, chromium (Cr), rhodium (Rh), or silver (Ag) may be used.

Figure 2A:
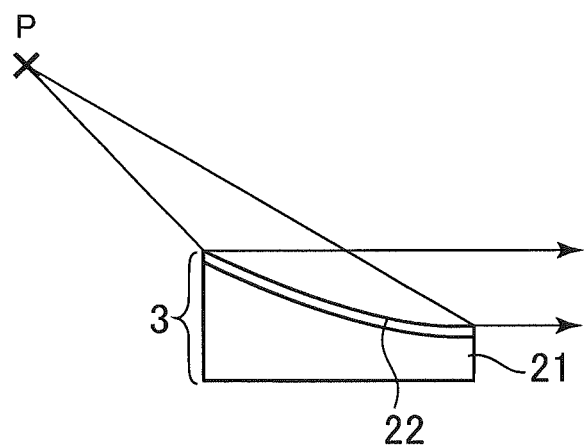
FIGS. 2A and 2B are schematic views illustrating a structure of a multilayer mirror according to the embodiment of the present invention.
Figure 2B:
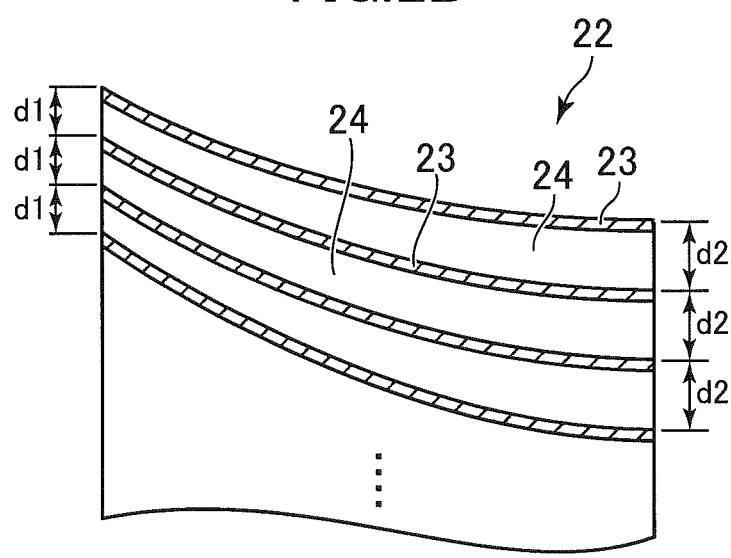

FIGS. 2A and 2B are schematic views illustrating a structure of the multilayer mirror 3 according to this embodiment. FIG. 2A is a sectional view of the multilayer mirror 3. The multilayer mirror 3 is formed of multiple layers 22 laminated on a surface of a substrate 21 made of silicon (Si). The multiple layers 22 have curved reflective surfaces, and the cross section of each curved reflective surface forms a parabola. Diffraction occurs in a plane of the cross section of the curved reflective surface, and hence the plane including the cross section serves as a scattering plane. The curved reflective surface is a curved surface extending while maintaining the shape of the parabola in a direction perpendicular to the scattering plane (direction of the thickness of the drawing sheet). Such a shape may be referred to as "parabolic surface". The curved reflective surface has a focal point P, and when the fine focal point of the X-ray source 2 is provided onto the focal point P, the X-ray reflected on the multilayer mirror 3 becomes a collimated X-ray in the scattering plane. This phenomenon is referred to as "collimation". For example, the collimated X-ray herein has a width of 1 mm to 3 mm. Note that, the X-ray reflected on the multilayer mirror 3 is herein referred to as "collimated X-ray", but in actuality, it is only necessary that the divergence (convergence) of the X-ray be suppressed to the extent that the desired resolution is obtained in the X-ray topographic image. In this case, the degree of collimation is 0.5 mrad, and is desirably 2 mrad or less, more desirably 1 mrad or less. FIG. 2B is a schematic view illustrating the cross sections of the multiple layers 22 of the multilayer mirror 3. The multiple layers 22 include heavy element layers 23 and light element layers 24 which are alternately deposited in a repeated manner. In this case, the heavy element layers 23 are made of tungsten (W), and the light element layers 24 are made of Si. However, the present invention is not limited thereto, and any appropriate materials may be applied depending on the desired characteristic X-ray. For example, the materials for the heavy element layers 23 and the light element layers 24 may be selected from among the combinations of iron (Fe) and carbon (C), nickel (Ni) and C, W and boron carbide ($B_4C$), and Mo and Si.

The distance between two identical layers adjacent to each other is assumed as a multilayer spacing "d". The multilayer spacing "d" refers to, for example, a spacing between the top surfaces of two adjacent heavy element layers 23. In the multiple layers 22, the multilayer spacing "d" gradually changes in a range from the incident side toward the opposite side, that is, from left to right in the cross section illustrated in FIG. 2B (horizontal direction of FIG. 2B). The multilayer spacing "d" of the multiple layers 22 is represented by "d1" at the left end and "d2" at the right end in the cross section illustrated in FIG. 2B. The multilayer spacing "d" gradually increases in the range from left to right of FIG. 2B, and "d2" is larger than "d1" (d1<d2). From the viewpoint of X-ray diffraction, the multilayer spacing "d" corresponds to a spacing between lattice planes of the crystal, and the multiple layers with the multilayer spacing "d" which changes from one position to the other is referred to as multiple layers with a "graded multilayer spacing". The multilayer spacing "d" at each position on the multiple layers 22 is determined based on the shape of the curved reflective surface and the wavelength of the X-ray to be reflected. That is, the multiple layers 22 have a multilayer spacing which corresponds to the wavelength of the characteristic X-ray, and the multilayer spacing of the multiple layers 22 changes with a gradient in the horizontal direction of FIG. 2B in conformity to the curved reflective surface. Ideally, it is desired that the cross section of the top surface of each heavy element layer 23 form a parabola with the focal point P as the focal point of the multilayer mirror 3. The multiple layers 22 have the graded multilayer spacing, and hence, when the X-ray containing the characteristic X-ray enters the multilayer mirror 3, the characteristic X-ray is reflected selectively, but the other X-rays are mostly absorbed by the multilayer mirror 3. This phenomenon is referred to as "monochromatization". Therefore, when the sample is placed in front of the collimated X-ray of FIG. 2A, the X-ray which enters the sample substantially contains only the characteristic X-ray, and the intensity of the other X-rays is attenuated greatly.

Note that, in this embodiment, the curved reflective surface of the multilayer mirror 3 maintains the shape of the parabola in the direction perpendicular to the scattering plane, but the present invention is not limited thereto. The shape of the parabola may be a curved surface extending while changing the shape of the parabola in the direction perpendicular to the scattering plane. In particular, when the curved reflective surface of the multilayer mirror 3 is a part of a side surface of a solid of revolution of the parabola, the X-ray reflected on the multilayer mirror 3 can be collimated also in a direction perpendicular to the cross section illustrated in FIG. 2A. In this case, the distances between the X-ray source 2 and the sample 100 and between the optical system 4 and the sample 100 can be set with high degrees of freedom, and thus a topography apparatus with higher positional resolution can be attained.

FIG. 3 is a schematic view illustrating the structure of the multilayer mirror 3 according to this embodiment. FIG. 3 illustrates the multilayer mirror 3 of FIG. 2A in a three-dimensional manner, and schematically illustrates the X-ray source 2 and the multilayer mirror 3. The X-ray radiated from the X-ray source 2 enters the multilayer mirror 3. The X-ray reflected on the multilayer mirror 3 is, as described above, only the desired characteristic X-ray that is monochromatized. Further, in the cross sectional plane illustrated in FIG. 2A (in the scattering plane), the X-ray is subjected to the collimation by the multilayer mirror 3 into a collimated X-ray. In a direction orthogonal to the cross section (scattering plane) (y-direction of FIG. 3), the X-ray remains a divergent X-ray along with the diversion of the X-ray radiated from the X-ray source 2. That is, the X-ray reflected on the multilayer mirror 3 is collimated in the scattering plane and diverged in the direction orthogonal to the scattering plane (y-direction). Such a beam is referred to as "fan beam". The fan beam of the desired characteristic X-ray enters the sample 100. Thus, unlike the conventional technology using a slit, the desired characteristic X-ray can be caused to enter the sample 100 over a wide area without using a geometric slit. Note that, FIG. 3 schematically illustrates an irradiation region IX of the sample 100. The length of the irradiation region IX of the sample 100 in the x-direction is referred to as "width of the fan beam" which enters the irradiation region IX, and the length of the irradiation region IX in the y-direction is referred to as "height of the fan beam".

The sample table 5 illustrated in FIG. 1 supports the sample 100, and includes a movement mechanism. The irradiation position of the incident X-ray can be adjusted by moving the sample 100. The movement mechanism herein refers to, for example, a stage capable of translation in the X-and Y-directions and rotation about the vertical axis. Through the movement of the sample 100 in a desired direction, an X-ray topographic image in the entire measurement region of the sample 100 can be taken while scanning the sample 100. In this case, the sample table 5 is adapted both to the transmission mode (Lang method) and to the reflection mode (double crystal method and Berg-Barrett method), and as described later, the arrangement of the X-ray source 2 and the X-ray detector 6 is determined to select one of the transmission mode and the reflection mode. In this manner, the X-ray topographic image can be taken.

The X-ray output from the multilayer mirror 3 is monochromatized to some extent, but in many cases, the X-ray contains characteristic X-rays having only a slight difference in wavelength, and for example, contains both the $K\alpha_1$ line and the $K\alpha_2$ line. However, the output X-ray is sufficiently collimated (for example, 1 mrad or less), and the angle of the incident X-ray with respect to the sample 100 is adjusted so that, due to the sample 100 as the single crystal, only the desired characteristic X-ray (for example, $K\alpha_1$ line) satisfies the diffraction condition and a high-definition topographic image can be obtained accordingly. The angle of the X-ray which enters the sample 100 from the optical system 4 is adjusted through the rotational movement of the first rotational driving system 7.

The X-ray detector 6 illustrated in FIG. 1 is, for example, a two-dimensional CCD camera, and is capable of detecting (taking) the X-ray topographic image. The X-ray detector 6 is not limited to the two-dimensional CCD camera, and may be any detector capable of taking the X-ray topographic image, such as an X-ray film and an imaging plate.

In the first rotational driving system 7 illustrated in FIG. 1, the fine focal point of the X-ray source 2 is provided onto the focal point of the curved reflective surface of the multilayer mirror 3, and the optical system 4 is adjusted so that the X-ray reflected on the multilayer mirror 3 irradiates the sample 100. Through the rotational movement of the first rotational driving system 7 with respect to the sample 100, the first rotational driving system 7 can move the X-ray source 2 and the optical system 4 into an angular arrangement suited to take an X-ray topographic image in any of the transmission mode and the reflection mode, and can further move with or without the scan the angular arrangement of the X-ray source 2 and the optical system 4 depending on the purpose of the measurement so that the X-ray which irradiates the sample 100 satisfies the desired diffraction condition with respect to the sample 100. That is, the first rotational driving system 7 can move the X-ray source 2 and the optical system 4 through the selection of one of the transmission geometry for transmissive measurement and the reflection geometry for reflective measurement. Note that, FIG. 1 illustrates an arrangement suited to the reflective measurement as a range A, and an arrangement suited to the transmissive measurement as a range B.

In the second rotational driving system 8 illustrated in FIG. 1, the X-ray detector 6 is arranged and adjusted at a position suited to detection of a diffracted X-ray generated through the sample 100. The second rotational driving system 8 can rotationally move with respect to the sample 100, and can move with or without the scan the angular arrangement of the X-ray detector 6 depending on the purpose of the measurement.

The control/analysis unit 9 illustrated in FIG. 1 controls X-ray topography measurement and analyzes measurement data thus obtained. In the X-ray topography measurement, the control/analysis unit 9 is configured to move the first rotational driving system 7 and the second rotational driving system 8, control the X-ray source 2 to radiate a predetermined X-ray, sequentially move the sample table 5 during the measurement so as to scan the entire measurement region of the sample 100, control the X-ray detector 6 to detect a diffracted X-ray generated through the sample 100, acquire measurement data from the X-ray detector 6, and store the measurement data thus acquired. In the X-ray topography data analysis, the control/analysis unit 9 is configured to combine the stored measurement data, to thereby generate an X-ray topographic image in the entire measurement region of the sample 100.

In the X-ray topography apparatus according to the present invention, without using a geometric slit, the fan beam (collimated X-ray) of the desired characteristic X-ray (monochromatic X-ray) can be used for the incident X-ray which enters the sample. The incident X-ray is the fan beam, and hence the width of the fan beam (length in the x-direction of FIG. 3) is maintained to be substantially constant irrespective of the distance between the multilayer mirror and the sample. Thus, when the length of the multilayer mirror (length from the left end to the right end of the cross section illustrated in FIG. 2A) is set larger, the width of the fan beam can be increased, and the width of the irradiation region of the incident X-ray which enters the sample 100 can be increased. Further, the fan beam diverges in the height direction (direction orthogonal to the scattering plane). When the distance between the multilayer mirror and the sample is set larger, the height of the fan beam (length in the y-direction of FIG. 3) can further be increased, and the height of the irradiation region of the incident X-ray which enters the sample can be increased. Thus, as compared to the conventional case, the range of the X-ray topographic image to be taken at a time can be increased, and accordingly the measurement time required for the measurement in the entire measurement range of the sample can be shortened. Note that, when the distance between the multilayer mirror and the sample is set larger, the brightness of the incident X-ray which enters the sample becomes lower accordingly, and hence, in view of the power output of the X-ray source, the distance between the multilayer mirror and the sample only needs to be determined so as to increase the irradiation region of the incident X-ray while securing a desired brightness of the incident X-ray.

Further, the monochromatization and collimation are performed using the multilayer mirror, and hence the incident X-ray which enters the sample is not only monochromatized by separating the characteristic X-ray Kα (for example, CuKα or MoKα) from the other X-rays, but also has a sufficient degree of collimation (divergence is suppressed sufficiently) so that the characteristic X-ray $K\alpha_1$ and the characteristic X-ray $K\alpha_2$ are sufficiently separated from each other through the diffraction on the sample 100. For example, the X-ray output from the multilayer mirror 3 used in this embodiment has a degree of collimation of 0.5 mrad. Through the monochromatization and collimation using the multilayer mirror, the X-ray topographic image taken in the X-ray topography apparatus 1 is, for example, an X-ray topographic image which is formed only from the characteristic X-ray $K\alpha_1$ without blurring. Further, as compared to the conventional Lang method, the X-ray topographic image has a sufficiently attenuated component of the continuous X-ray contained in the incident X-ray which enters the sample, and hence the obtained X-ray topographic image is substantially unaffected by the background due to the Laue diffraction of the continuous X-ray.

The conventional X-ray topography apparatus is required to use a geometric slit, and the degree of freedom in designing the apparatus is limited due to the arrangement of the slit. In contrast, the X-ray topography apparatus 1 according to the present invention does not use a geometric slit, and hence the degree of freedom in designing the apparatus becomes higher. For example, as illustrated in FIG. 1, in the X-ray topography apparatus 1 according to this embodiment, the first rotational driving system 7 can move the X-ray source 2 and the optical system 4 into the arrangement in the transmission mode or the reflection mode. Further, the first rotational driving system 7 can move the X-ray source and the optical system so that the X-ray satisfies the desired diffraction condition with respect to the sample. In the conventional Lang X-ray topography apparatus, the slit is arranged in the vicinity of the sample, and thus it is extremely difficult to move the optical components such as the slit along with the movement of the X-ray source, but the present invention produces a remarkable effect therefor.

It is desired that the multilayer mirror used for the X-ray topography apparatus according to the present invention have a high surface accuracy. The surface accuracy (low figure error) of the multilayer mirror 3 according to this embodiment is 4 seconds of arc (arcsec) (=4/3, 600 degrees), and is desirably 10 arcsec or less, more desirably 5 arcsec or less. The surface accuracy (surface figure error from the ideal surface) is herein defined as an inclination angle 5 of the most inclined (steepest) part of an actual surface with respect to an ideal surface of the multilayer mirror that is inclined with respect to the actual surface. When the surface accuracy of the multilayer mirror is low, imperfection of the multilayer mirror is superimposed on the X-ray topographic image obtained through the measurement, and it becomes difficult to distinguish whether an image of a defect shown in the X-ray topographic image results from the defect in the lattice of the sample or from the surface accuracy of the multilayer mirror. When a multilayer mirror having a high surface accuracy is used, on the other hand, the X-ray topographic image can be obtained with higher accuracy.

Further, the optical system 4 of the X-ray topography apparatus 1 according to this embodiment may further include a single crystal monochromator. The single crystal monochromator is arranged close to the output end of the optical system 4 with respect to the multilayer mirror 3 illustrated in FIG. 1. That is, the single crystal monochromator is arranged between the multilayer mirror 3 and the sample 100. When a single crystal monochromator which corresponds to the wavelength of the predetermined characteristic X-ray is arranged (double crystal method), the degree of collimation of the X-ray which enters the sample 100 can further be increased. In particular, such arrangement is preferred in a case where an X-ray topographic image with higher strain sensitivity needs to be taken.

The X-ray topography apparatus according to the embodiment of the present invention has been described above. The present invention is not limited to the embodiment described above, and is widely applicable to an X-ray topography apparatus, which uses an X-ray source for radiating an X-ray from a fine focal point and a multilayer mirror to form an incident X-ray which enters a sample into a fan beam, thereby enabling real-space mapping of the sample in a region irradiated with the X-ray.

While there have been described what are at present considered to be certain embodiments of the invention, it will be understood that various modifications may be made thereto, and it is intended that the appended claims cover all such modifications as fall within the true spirit and scope of the invention.

What is claimed is:

1. An X-ray topography apparatus, comprising:
    an X-ray source for radiating an X-ray from a fine focal point, the X-ray containing a predetermined characteristic X-ray;
    an optical system comprising a multilayer mirror with a graded multilayer spacing which corresponds to the predetermined characteristic X-ray, the optical system being configured to cause the X-ray reflected on the multilayer mirror to enter a sample; and
    an X-ray detector for detecting a diffracted X-ray, which is generated through the sample,
    wherein the multilayer mirror comprises a curved reflective surface having a parabolic cross section, and the fine focal point of the X-ray source is provided onto a focal point of the curved reflective surface, and the optical system is structured to cause the X-ray to be collimated in a first direction and enter the sample by reflection on the multilayer mirror; and
    wherein the optical system is structured to cause the X-ray to be diverged in a second direction intersectional to the first direction to enter the sample by reflection on the multilayer mirror.

2. The X-ray topography apparatus according to claim 1, further comprising a rotational driving system having the X-ray source and the optical system arranged thereon, the rotational driving system being rotationally movable with respect to the sample,
    wherein the rotational driving system is configured to move the X-ray source and the optical system through selection of one of a transmission geometry for transmission topography and a reflection geometry for reflection topography, and to further move the X-ray source and the optical system in the selected one of the transmission geometry and the reflection geometry so that the X-ray satisfies a desired diffraction condition with respect to the sample.

3. The X-ray topography apparatus according to claim 1, wherein the optical system further comprises a single crystal monochromator arranged between the multilayer mirror and the sample, the single crystal monochromator corresponding to a wavelength of the predetermined characteristic X-ray.

4. The X-ray topography apparatus according to claim 1, wherein the multilayer mirror has a surface accuracy of 10 arcsec or less.

5. The X-ray topography apparatus according to claim 1,
   wherein the optical system is configured to cause the X-ray entering the sample to be monochromatized to the predetermined characteristic X-ray by reflection on the multilayer mirror.

6. The X-ray topography apparatus according to claim 1,
   wherein the curved reflective surface of the multilayer mirror maintains a shape of the parabolic cross section in the second direction.

* * * * *